United States Patent [19]

Chiprich et al.

[11] Patent Number: 5,614,217
[45] Date of Patent: Mar. 25, 1997

[54] CAPSULE SHELL FORMULATION TO PRODUCE BRITTLE CAPSULES

[75] Inventors: Timothy B. Chiprich; Michael T. Hoylman, both of St. Petersburg; Norman S. Stroud, Safety Harbor, all of Fla.

[73] Assignee: R.P. Scherer Corporation, Troy, Mich.

[21] Appl. No.: 482,775

[22] Filed: Jun. 7, 1995

[51] Int. Cl.$^6$ .................................. A61K 9/48
[52] U.S. Cl. .......... 424/451; 424/452; 424/454; 424/455; 424/456; 514/962; 514/778; 514/781; 514/782; 514/777; 514/783; 514/772.3
[58] Field of Search ............................. 424/451, 452, 424/454, 455, 456, 453

[56] References Cited

U.S. PATENT DOCUMENTS

| | | | |
|---|---|---|---|
| 3,515,070 | 6/1970 | Cutler et al. | 102/60 |
| 3,556,916 | 1/1971 | Levey et al. | 161/283 |
| 3,592,945 | 7/1971 | Engelkin et al. | 252/316 |
| 3,627,695 | 12/1971 | Scarpelli et al. | 252/316 |
| 3,865,603 | 2/1975 | Szymanski et al. | 106/130 |
| 4,055,554 | 10/1977 | Helmstetter | 260/117 |
| 4,278,633 | 7/1981 | Fujii | 264/134 |
| 4,350,679 | 9/1982 | Mizuno et al. | 424/38 |
| 4,432,768 | 2/1984 | Brown et al. | 604/200 |
| 4,500,358 | 2/1985 | Mayer et al. | 424/15 |
| 4,784,506 | 11/1988 | Koreska et al. | 401/132 |
| 4,865,056 | 9/1989 | Tamsoki et al. | 131/337 |
| 4,935,243 | 6/1990 | Borkan et al. | 424/441 |
| 4,957,385 | 9/1990 | Weinstein | 401/132 |
| 5,133,458 | 7/1992 | Miller | 206/530 |
| 5,200,149 | 4/1993 | Fisher | 422/61 |
| 5,213,860 | 5/1993 | Laing | 428/36.92 |
| 5,282,572 | 2/1994 | Fuller | 239/56 |

*Primary Examiner*—James M. Spear
*Attorney, Agent, or Firm*—Banner & Witcoff, Ltd.

[57] ABSTRACT

A gelatin capsule that is generally resistant to humidity having a non-hygroscopic plasticizer and an elasticity reducing gelatin extender in the formulation of the gelatin capsule shell. The capsule is capable of being manufactured on conventional rotary die encapsulation devices and can readily hold liquid fill materials. The capsule is breakable with manual pressure.

23 Claims, 1 Drawing Sheet

CAPSULE SHELL FORMULATION TO PRODUCE BRITTLE CAPSULES

BACKGROUND OF THE INVENTION

1. Field of the Invention

This invention relates to a gelatin capsule formulation that provides a brittle shell that can be manually broken for the release of the contents therein. More particularly, it relates to a gelatin capsule formulation that utilizes a non-hygroscopic plasticizer to plasticize the gelatin in the formulation to provide a shell that after drying resists moisture and remains brittle but that is strong enough to be manufactured in a traditional rotary die encapsulation device.

2. Brief Description of the Prior Art

Breakable capsules were developed in the 1940's for the purpose of delivering yellow dye to add coloring to margarine so it would look similar to butter. The breakable capsule was produced by using a glycerine plasticized gelatin capsule that was treated with formaldehyde to cross link the gelatin. Other agents are used to harden the gelatin to provide the moisture resistance and be brittle so as to allow breaking of the capsule.

U.S. Pat. No. 4,055,554 discloses the use of chemically modified dialdehyde polysaccharides to enhance the strength of the gelatin compositions used to produce capsules which have been extended with starch or dextrin.

U.S. Pat. No. 4,350,679 discloses a coating of film of carnauba wax on a soft gelatin capsule to provide strength to the capsule shell. The carnauba wax inhibits the absorption of water into the shell formulation and thus provides moisture resistance to the shell.

U.S. Pat. No. 3,592,945 discloses a protective coating on gelatin capsules comprising a copolymer of methacrylic acid and methylmethacrylate having a molecular weight between 110,000 and 160,000. A softener such as dibutyphthalate and castor oil may be added.

When capsules are coated or chemically treated, the ease of manufacture is reduced and costs increase. There is a need for a gelatin capsule that has enough strength to hold liquid filling material and withstand the manufacturing process on a conventional rotary die capsule making device but that after drying is brittle and can be easily broken open manually to release the contents therein.

SUMMARY OF THE INVENTION

The brittle gelatin capsule of the invention comprises about 30% to about 60% gelatin by weight, about 5% to about 15% water by weight, about 15% to about 35% by weight non-hygroscopic plasticizer and about 8% to about 30% by weight elasticity reducing gelatin extender. The capsule can be manufactured on conventional rotary die encapsulation devices and readily hold liquid fill materials. Most conveniently, the finished capsule remains breakable with manual pressure in changing environmental conditions without the need of special treatments or moisture resistant packaging.

DETAILED DESCRIPTIONS OF THE PREFERRED EMBODIMENTS

Figure 1:
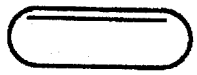
FIG. 1 is a side view of an embodiment of the present invention with no score lines.

Conventional soft gelatin capsules are strong and elastic.

The capsule of the present invention must have its gel strength and elasticity reduced to provide a finished dried capsule which is brittle so that it can be broken using finger pressure and does not soften as typical soft gelatin capsules do upon exposure to humidity. The capsule also must be strong enough so that it can be made on a conventional rotary die encapsulation device without breaking. It would not be economical to produce brittle gelatin capsules on other conventional capsule making devices.

In accordance with the present invention, the formulation for the novel capsule is modified to reduce the gel strength and elasticity by replacing a portion of the gelatin with starch in the formulation which reduces the elasticity of the gel. In this regard, the breakable characteristic of the capsule only functions if the plasticizer level is kept low, that is below about 0.5:1 plasticizer to solids and that the capsules are not exposed to humidity. Softening of gelatin capsules normally occurs at about 40% relative humidity or higher. Conventional soft gelatin capsules are plasticized with water and hygroscopic polyols.

Typically, capsules pick up moisture in proportion to their glycerin (which is a hygroscopic polyol) and gelatin content. Therefore, in the present invention, non-hygroscopic plasticizers must be used as well as elasticity reducing gelatin extenders. A non-hygroscopic plasticizer is used to plasticize the gelatin in the conventional capsule formulation. It does not absorb moisture at the rate of conventional plasticizers. When this type of a plasticizer is utilized to plasticize the gelatin in the formulation, a gelatin ribbon is produced that performs well in the rotary die encapsulation device with no special manufacturing requirements that results in finished capsules that retain their integrity for long periods of time at high relative humidity, for example, 70% relative humidity. Some of the non-hygroscopic plasticizers that may be used in the present invention include maltitol, maltitol syrup, partially dehydrated hydrogenated glucose syrups, hydrogenated starch hydrolysate and polyhydric alcohols having an equilibrium relative humidity of greater than or equal to 80% such as the high molecular weight polyethylene glycols. A preferred non-hygroscopic plasticizer is maltitol syrup. The non-hygroscopic plasticizer may be present in the formulation of the present invention in amounts ranging from about 15 to about 35% by weight and most preferably, in amounts ranging from about 25 to about 29% by weight.

The elasticity reducing gel extender used in the formulation of the present invention replaces a portion of the gelatin component of the formulation, and may consist of starch, starch derivatives such as high amylose starch, oxidized starch, esterified starch, acid-thinned starch, etherified starch, hydrolyzed starch, hydrolyzed and hydrogenated starch, enzyme treated starch, and modified celluloses or other natural or modified natural biopolymers such as bacterial polysaccharides, vegetable gums, or other exudates including alginates, carrageenans, guar gum, gum arabic, gum ghatti, gum karaya, gum tragacanth, pectins, tamarind gum, xanthan gum, and dextrans as well as synthetic polymers such as carbon chain polymers of the vinyl and acrylic types as well as heterochains of the polyoxide and polyamine types including polyethylene oxide, polypropylene oxide, polyoxymethylene, polytrimethylene oxide, block copolymers of ethylene oxide, block copolymers of polyethylene oxide, polyvinyl methyl ether, polyethylene imine, polyacrylic acid, polyacrylamide, polymethacrylic acid, polymethacrylamide, poly(N,N-Dimethylacrylamide), poly(N-Isopropylacrylamide), poly(N-Acrylylglycinamide), poly(N-Methyacrylyglycinamide), acrylic copolymers, polyvinyl alcohol polyvinylacetate, polyvinyl acetate-co-vinyl alcohol, polyvinylpyrrolidone, N-Methylpyrrolidone, N-Ethylpyrrolidone, N-Vinylpyrrolidone, sarcosine anhydride, polyvinyloxazolindone, and polyvinylmethyloxazolidone. The starch or other elasticity reducing gel extender may be added into the formulation in amounts ranging from about 8% to about 30% by weight and most preferably in amounts ranging from about 10% to about 16% by weight.

The gelatin used in the formulation of the present invention may be a conventional gelatin or a chemically modified gelatin such as succinated gelatin, acylated gelatins, phthalated gelatins, carbanylated gelatins and phenol carbanylated gelatins. The gelatin of the formulation of the invention is present in amounts ranging from about 30% to about 60% by weight and most preferably in amounts ranging from about 50% to about 54% by weight. The capsules of the present invention are formulated to hold any gelatin compatible fill material, particularly liquid fill material. The gelatin capsule provides a vehicle for dispensing pre-measured medicaments, cosmetic, recreational or industrial materials, dissolved or dispersed in the vehicle. For example, the gelatin capsule of the present invention may be a disposable applicator for such products as topical medications, such as anesthetics, antiseptics, and poison ivy protectants, nail color remover, and marker liquids. The capsule of the present invention is manually breakable with finger pressure so that the liquid fill material can be applied where needed.

The biodegradable nature of the gelatin capsule provides for consumer acceptance of disposable products. Since the capsules of the present invention contain a non-hygroscopic plasticizer, they require less moisture resistance in their packaging than traditional soft gelatin capsules and therefore provide cost efficiency because of less expensive packaging materials being required.

The capsule of the present invention when filled with a compatible liquid material may be wrapped in a swab or sheath of fabric upon which the liquid fill material may be absorbed when the capsule is manually broken open. The swab or sheath of fabric may then be used as an applicator to dispense the liquid fill material where needed. The gelatin formula of the present invention could also be used with a powdered fill material to make capsules using a conventional encapsulation device such as an Accogel type encapsulation machine developed by the Lederle Laboratories of the American Cyanamid Company that accurately fills powdered dry solids into soft gelatin capsules.

The capsule of the present invention may further be enhanced in terms of its breakability by using conventional techniques to score the capsule. The scoring of the capsule helps to both control the breaking point and to reduce the pressure needed to induce breakage of the capsule to release the fill material contained therein.

FIG. 1 shows a representation of an unscored breakable capsule. The capsule may be held by the index and thumb of each hand and with pressure applied by the thumbs, the capsule will easily break to release its contents.

Figure 2:
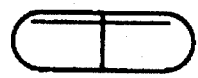
FIG. 2 is a side view of an embodiment of the present invention with a single score line.

FIG. 2 is a representation of a breakable capsule with a single score line. The score line provides a focal point for applying pressure to the capsule so that it may be readily broken for release of its contents.

Figure 3:
FIG. 3 is a side view of an embodiment of the present invention with multiple score lines.

FIG. 3 is a representation of a capsule with multiple score lines.

Figure 4:
FIG. 4 is a side view of an embodiment of the present invention with multiple score lines on the end of the capsule that is intended to be broken.

FIG. 4 is a representation of a breakable capsule in the shape of an ampule. Score lines are present at the head of the ampule to direct the user to breaking the ampule at that location. Other forms of capsules can be made in accordance with the present invention, and the forgoing designs of the capsules are in no way intended to be limiting.

EXAMPLE 1

TABLE I

| Ingredient | %w\w Preferred | Most Preferred |
| --- | --- | --- |
| Gelatin, NF | 30–60 | 50–54 |
| Starch | 8–30 | 10–16 |
| Maltitol Syrup | 15–35 | 25–29 |
| Purified Water | 5–15 | 8–12 |

The above listing of the ingredients and preferred and most preferred ranges of amounts of the ingredients are utilized in the finished, dried shell of the capsules of the present invention. In preparing the capsules of the present invention, the amount of water shown in Table I for the finished product is modified. The amount of water should be sufficient to produce a flowable gelatin mass while in a molten state at a viscosity of about 5,000 to about 25,000 cps at approximately 140° F. During drying, water is lost so that the final parameters of formulation are as shown in Table I.

The gelatin formula of the present invention is prepared using conventional techniques. The gelatin, starch, maltitol syrup, and water are placed into a suitable mixer such as a pony mixer (or alternatively into a jacketed mixer-melter vessel with mixing and vacuum capabilities) and are mixed until the liquids are absorbed into the solids and are considered "crumbed" (meaning fluffy swollen pieces). The crumbed gelatin formula components are then transferred into a melting tank (unless the mixer-melter technique is utilized in such instance the transfer of the components are not necessary). The crumbed gelatin formula components are then melted under vacuum at approximately 29.5" HG at 140°–200° F. until molten which may take from 1 to 5 hours, depending upon the quantity of the materials.) The gel mass is then transferred to a holding tank and maintained at approximately 140° F. until introduction into a rotary die encapsulation device.

The mass of gelatin is fed into a standard rotary die process soft gelatin encapsulation device manufactured by R. P. Scherer. The gelatin is passed through heated tubes into spreader boxes which spread the gel onto cold rotating drums forming a gelatin ribbon. If scoring of the capsules is desired, texturizing rollers are used at this time to place lines on the ribbon in the appropriate place for facilitating the breaking of the capsule when dried. The gel ribbon is then fed through lubricated guided rollers which feed the ribbon between an injection wedge and die rolls.

The fill material, which is compatible with the gelatin, is injected through the heated wedge while the ribbon goes through the die rolls. The heat of the wedge along with the pressure of the dies cause capsules to be simultaneously cut, filled and sealed. The capsules are then transferred by conveyor belt into drying tumblers to begin the drying process. The capsules are transferred automatically through the drying tumbler and are spread on trays. The trayed capsules are then placed in a controlled humidity area (<15% Relative Humidity) to finish drying. The capsules lose water and come to equilibrium with the humidity of the drying area. At this time the capsules become brittle and breakable. The capsules can then be exposed to humidities up to 70% RH without softening. If the capsules are exposed to humidities of greater than 70% RH they soften (over a few hours time) and become unbreakable until they are then exposed to humidities of less than 70% RH for a short period of time at which time they become breakable again.

While this invention has been described with reference to certain specific embodiments, it will be recognized by those skilled in the art that many variations are possible without departing from the scope and spirit of the invention, and it will be understood that it is intended to cover all changes and modifications of the invention, disclosure and for the purpose of illustration, which do not constitute departures from the spirit and scope of the invention.

The embodiments of the invention in which an exclusive property or privilege is claimed are defined as follows:

1. A humidity resistant gelatin capstile comprising:
   a fill material;
   a gelatin shell encapsulating the fill material; the gelatin capstile comprising about 30 to about 50% gelatin, about 5 to about 15% by weight water, about 15% to about 35% by weight maltitol syrup, and about 8% to about 30% by weight elasticity reducing gelatin extender.

2. The capstile of claim 1 wherein the elasticity reducing gel extender is selected from the group consisting of starch, amylose starch oxidized starch, esterified starch, acid-thinned starch, etherified starch, hydrolyzed starch, hydrolyzed starch, hydrogenated starch, enzyme treated starch, cellulose and modified cellulose.

3. The capsule of claim 1 wherein the gelatin that is incorporated into the capsule shell is selected from the group consisting of conventional gelatin and chemically modified gelatins.

4. The capsule of claim 1 that is capable of being manually breakable to release the contents thereof.

5. A humidity resistant gelatin capsule comprising:
   a liquid fill material;
   a gelatin shell encapsulating the fill material; the gelatin capsule comprising about 30 to about 50% gelatin, about 5 to about 15% by weight water, about 15% to about 35% by weight maltitol syrup, and about 8% to about 30% by weight elasticity reducing gelatin extender.

6. The capsule of claim 5 wherein the elasticity reducing gel extender is selected from the group consisting of starch, amylose starch, oxidized starch, esterified starch, acid-thinned starch, etherified starch, hydrolyzed starch, hydrolyzed starch, hydrogenated starch, enzyme treated starch, cellulose and modified celluloses.

7. The capsule of claim 1 wherein the elasticity reducing gel extender is selected from the group consisting of natural and modified natural biopolymers.

8. The capsule of claim 7 wherein the elasticity reducing gel extender is selected from the group consisting of bacterial polysaccharides, vegetable gums and vegetable exudates.

9. The capsule of claim 8 wherein the elasticity reducing gel extender is selected from the group consisting of olginates, carraganans, guar gum, gum arabic, gum ghatti, gum karaya, gum tragacanth, pectin, tamarind gum, xanthan gum and dextran.

10. The capsule of claim 1 wherein the elasticity reducing extender is a synthetic polymer.

11. The capsule of claim 10 wherein the elasticity reducing extender is selected from the group consisting of vinyl and acrylic carbon chain polymers.

12. The capsule of claim 10 wherein the elasticity reducing gel extender is selected from the group consisting of polyoxide and polyamine heterochains.

13. The capsule of claim 12 wherein the elasticity reducing gel extender is selected from the group consisting of polyethylene oxide, polypropylene oxide, polyoxymethylene, polyrimethylene oxide, block copolymers of ethylene oxide, block copolymers of polyethylene oxide, polyvinyl methyl ether, polyethylene irainc, polyacrylic acid, polyacrylamide, polymethacrylic acid, polymethacrylamide, poly (N,N-Dimethylacrylamide), poly (N-Isopropylacrylamide), poly (N-Acrylylglycinaminde), poly (N-Methyacrylyglycinamide), acrylic copolymers, polyvinyl alcohol polyvinylacetate, polyvinyl acetate-co-vinyl alcohol, polyvinylpyrrolidone, N-Methylpyrrolidone, N-Ethylpyrrolidone, N-Vinylpyrrolidone, sarcosine anhydride, polyvinyloxazolindone, and polyvinylmethyloxazolidone.

14. The capsule of claim 5, wherein the elasticity reducing gel extender is selected from the group consisting of natural and modified natural biopolymers.

15. The capsule of claim 14 wherein the elasticity reducing gel extender is selected from the group consisting of bacterial polysaccharides, vegetable gums and vegetable exudates.

16. The capsule of claim 15 wherein the elasticity reducing gel extender is selected from the group consisting of olginates, carraganans, guar gum, gum arabic, gum ghatti, gum karaya, gum tragacanth, pectin, tamarind gum, xanthan gum and dextran.

17. The capsule of claim 5 wherein the elasticity reducing extender is a synthetic polymer.

18. The capsule of claim 17 wherein the elasticity reducing extender is selected from the group consisting of vinyl and acrylic carbon chain polymers.

19. The capsule of claim 17 wherein the elasticity reducing gel extender is selected from the group consisting of polyoxide and polyamine heterochains.

20. The capsule of claim 19 wherein the elasticity reducing gel extender is selected from the group consisting of polyethylene oxide, polypropylene oxide, polyoxymethylene, polyrimethylene oxide, block copolymers of ethylene oxide, block copolymers of polyethylene oxide, polyvinyl methyl ether, polyethylene imine, polyacrylic acid, polyacrylamide, polymethacrylic acid, polymethacrylamide, poly (N,N-Dimethylacrylamide), poly (N-Isopropylacrylamide), poly (N-Acrylylglycinaminde), poly (N-Methyacrylyglycinamide), acrylic copolymers, polyvinyl alcohol polyvinylacetate, polyvinyl acetate-co-vinyl alcohol, polyvinylpyrrolidone, N-Methylpyrrolidone, N-Ethylpyrrolidone, N-Vinylpyrrolidone, safcosine anhydride, polyvinyloxazolindone, and polyvinylmethyloxazolidone.

21. The capsule of claim 15 wherein the gelatin that is incorporated into the capsule shell is selected from the group consisting of conventional gelatins and chemically modified gelatins.

22. A humidity resistant gelatin capsule that is scored to facilitate breaking to release the contents therein comprising:
   a fill material;

a gelatin shell encapsulating the fill material; the gelatin capsule comprising about 30 to about 50% gelatin, about 5 to about 15% by weight water, about 15% to about 35% by weight maltitol syrup, and about 8% to about 30% by weight elasticity reducing gelatin extender.

23. A humidity resistant gelatin capsule capable of being manufactured in a standard rotary die soft gelatin encapsulation device comprising:

a fill material;

a gelatin shell encapsulating the fill material; the gelatin capsule comprising about 30 to about 50% gelatin, about 5 to about 15% by weight water, about 15% to about 35% by weight maltitol syrup, and about 8% to about 30% by weight elasticity reducing gelatin extender.

* * * * *